United States Patent [19]

Couch et al.

[11] Patent Number: 5,448,609
[45] Date of Patent: Sep. 5, 1995

[54] METHOD AND APPARATUS FOR COMBINING CT SCANNER SYSTEM DETECTOR OUTPUTS

[75] Inventors: John L. Couch, San Francisco; Horst Bruening, Walnut Creek; Guenter Hahn, Menlo Park, all of Calif.

[73] Assignees: Siemens Aktiengesellschaft, Munich, Germany; Imatron, Inc., So. San Francisco, Calif.

[21] Appl. No.: 107,806

[22] PCT Filed: Jun. 28, 1993

[86] PCT No.: PCT/US93/06116

§ 371 Date: Aug. 20, 1993

§ 102(e) Date: Aug. 20, 1993

[87] PCT Pub. No.: WO94/00850

PCT Pub. Date: Jan. 6, 1994

Related U.S. Application Data

[63] Continuation-in-part of Ser. No. 905,009, Jun. 26, 1992.

[51] Int. Cl.[6] ............................... H05G 1/60
[52] U.S. Cl. ............................... 378/19; 378/4
[58] Field of Search ........................ 378/4, 19

[56] References Cited

U.S. PATENT DOCUMENTS

| | | | |
|---|---|---|---|
| 4,066,900 | 1/1978 | LeMay | 250/360 |
| 5,046,158 | 9/1991 | Goern | 341/137 |
| 5,142,286 | 8/1992 | Ribner et al. | 341/143 |
| 5,203,335 | 4/1993 | Noujaim et al. | 128/661.01 |
| 5,287,107 | 2/1994 | Gampell et al. | 341/137 |

*Primary Examiner*—Craig E. Church
*Attorney, Agent, or Firm*—Lawrence C. Edelman

[57] ABSTRACT

In a computed tomography X-ray system, the number of A/D converters required to digitize detector output signals is reduced without degrading the resultant tomographic image. This hardware reduction results from combining certain detector output signals into a pseudo detector having a single output. The detector output signals thus combined represent data corresponding to X-ray beams having substantially the same Radon radius. Preferably such X-ray beams also traverse substantially the same region of the CT system's reconstruction circle. Where the pseudo detector includes the output signals read from N sequentially scanned detectors $D_i$, where $i=1$ denotes the first read detector and $i=N$ the last read detector, the output of each detector $D_i$ is delayed a time $(N-i)\tau$, and the thus delayed outputs are summed together to provide the pseudo detector output. In the above relationship, $\tau$ is the interval between reading adjacent detectors $D_i$ and $D_{i+1}$. A pseudo detector may also be created in a system having one detector that is sequentially repositioned to N locations. Because each pseudo detector includes N detector output signals, and provides a single pseudo detector output, the number of signals requiring downstream digitizing and/or other processing is reduced by a factor N. The output signal from each pseudo detector may then be multiplexed, digitized or otherwise downstream processed as in the prior art.

11 Claims, 4 Drawing Sheets

METHOD AND APPARATUS FOR COMBINING CT SCANNER SYSTEM DETECTOR OUTPUTS

This application is a continuation in part of Ser. No. 07/905,009 filed Jun. 26, 1992.

FIELD OF THE INVENTION

The present invention relates generally to computed tomography X-ray systems, and more particularly to methods and apparatus for reducing the complexity of the analog-to-digital processors and the number of downstream channels required to process x-ray detector output signals in such systems.

BACKGROUND OF THE INVENTION

Early in this century, the Austrian mathematician J. Radon demonstrated that a two-dimensional slice of a three-dimensional object may be reproduced from an infinite set of all of its projections. Computed tomography ("CT") X-ray systems generate an infinite set of X-ray beam projections through an object to be examined. The resultant detected X-ray data are computer processed to reconstruct a tomographic image-slice of the object.

More specifically, CT systems subject the object under examination to one or more pencil-like X-ray beams from all possible directions. X-ray beams passing through the object are attenuated by various amounts, depending upon the nature of the object traversed (e.g., bone, tissue, metal). One or more X-ray detectors, disposed on the far side of the object, receive these beams and provide analog output signals proportional to the strength of the incoming X-rays. Each detector output is then digitized and computer processed to help produce an image of a slice of the object.

For an ideally reconstructed image, a CT system would have an infinitely large number of extremely tiny closely-spaced detectors (or fewer detectors repositionable to an infinite number of very closely spaced locations). Because of limitations imposed by economics and hardware, practical CT systems process X-ray beam data from hundreds or thousands of detectors (or detector positions). However, the cost of analog-to-digital ("A/D") conversion of the output of hundreds or thousands of detectors can be prohibitive. The present invention discloses an apparatus and method for reducing the complexity of A/D converters required by CT systems, as well as the number of digitized information channels to be computer processed, without substantial degradation of the image produced.

At this juncture it is helpful to briefly overview the various types of CT X-ray scanner systems that have been developed, to appreciate better the problems associated with obtaining sufficient data to provide a meaningful output image.

A "first generation" CT scanner configuration is schematically depicted in FIG. 1A, and includes a single X-ray source (S), and a single detector (D), both of which move in a translate-rotate fashion (indicated by arrows T, R) relative to the object under examination (O). The translate-rotate movement causes the X-ray beam B to pass through the object O from all directions, with the moving detector D providing an analog output signal at many detector positions responsive to the various beam paths. A signal processing mechanism (SP) digitizes the output of D and ultimately reconstructs an image of a slice of the object O.

For ease of illustration, FIG. 1A (and indeed FIGS. 1B, 1C, 1D) depicts detector D and source S rotating with an equal radius about the object O, but in practice these radii need not be equal. Further, as is also the case with FIGS. 1B, 1C and 1D, relative motion between the object and the source and detector is all that is required, and in some applications the detector D and source S are stationary and the object O is rotated. For example, some industrial CT scanners that image large objects (an airplane wing, for example) require a source S which is too large to move, and therefore instead move the object relative to a stationary source and detector.

FIG. 1B depicts a second generation scanner wherein a source S emits an X-ray fan beam B, portions of which pass through the object O and are detected by a single detector D, where both source and detector move in a translate-rotate fashion. Because a fan beam of X-rays is used, the system of FIG. 1B can complete a scan more quickly than the system of FIG. 1A. For example, if the fan beam B comprises N rays, object O may be scanned N times faster than the first generation system of FIG. 1A wherein there is but one ray. For ease of illustration, FIG. 1B depicts a small number of rays, but fan beam B actually includes a continuum of rays. Again, it is understood that detector D and source S need not be equidistant from the object O, and that relative motion between the object and the source and detector, is all that is required. A signal processing mechanism (SP) digitizes the detector output and provides an image of a slice of the object O.

FIG. 1C depicts a third generation CT scanner system having a point X-ray source S and multiple detectors $D_i$ arranged in an arc, where point source S and the array of detectors $D_i$ rotate relative to the object O, but there is no translational movement. Conceptually if the single detector of FIG. 1A could be relatively rotated in an arc to various detector positions corresponding to $D_i$, it could serve as the plurality of detectors shown in FIG. 1C. Again, the radii of relative motion are drawn equal for ease of illustration only. A signal processing mechanism (SP) digitizes the detector outputs and provides an image of a slice of the object O. U.S. Pat. No. 4,630,202 to Mori (Dec. 16, 1986) describes a conventional third generation CT scanner.

FIG. 1D depicts a fourth generation CT scanner system as including a source S that emits an X-ray fan beam B and an array of detectors $D_i$, wherein the source S rotates relative to the object O, the detector array is stationary, and no translational movement of source or detectors occurs. Again it is understood that the detector array and X-ray source are drawn as being equidistant from the object O merely for ease of illustration. A signal processing mechanism (SP) digitizes the detector outputs and provides an image of a slice of the object O.

FIG. 1E depicts in greater detail a fourth generation scanning electron beam CT system such as described generally in U.S. Pat. No. 4,352,021 to Boyd, et al., (Sep. 28, 1982). In the CT system 10 of FIG. 1E, there is a housing chamber 12 wherein an electron beam 14 is generated and caused by a beam optics assembly 16 to scan an arc-like typically tungsten target 18 located within chamber 12's front lower portion 20. Upon being struck by the electron beam, the target emits a moving fan-like beam of X-rays 22. At least some of these X-ray beams pass through a region of object 24 and then register upon a region of a detector array 26 located generally diametrically opposite that portion of target 18 struck by the electron beam 14. The detector array includes a relatively large number of detectors D (perhaps 2,000–5,000) that sequentially receive at least a portion of the moving beam of X-rays. Each detector's output is an analog signal typically representing a few nA of current, which signal is passed through a current-to-voltage converter (not shown) to yield an analog signal of perhaps several hundred mV. Preferably each detector output is lowpass filtered (filters not shown) to remove frequency components higher than about 25 KHz. The analog detector outputs are then digitized using analog to digital ("A/D") converters.

To reduce the number of A/D converters required (and thus the number of digitized signal channels requiring computer processing downstream), blocks of analog detector outputs are typically multiplexed. The multiplexed outputs are then digitized using A/D converters, with fewer A/D converters required because of the multiplexing. These multiplexing and converting steps are carried out by the Digital Acquisition System (DAS) depicted generally in FIG. 1E by box 30. The digitalized signal channels from the A/D converters are then coupled to a computer system 32 where they are extensively processed to produce an image of a slice of the X-rayed subject on a high resolution video monitor 34. Typically computer system 32 also controls reading of the various detectors, electron beam scanning, and repositioning of the X-rayed subject 24. With reference to FIGS. 1A–1D, the signal processing mechanism (SP) depicted therein may be thought of as including elements 30, 32 and 34 as depicted in FIG. 1E.

FIG. 1E helps demonstrate that in reconstructing a tomographic image from X-ray detector data, it is unimportant how the X-ray beams were caused to traverse the object O. For example, while FIG. 1E depicts a scanning electron beam system, one could just as easily mount an X-ray generator on a mechanical gantry and rotate the gantry (which could include the detector array) about the subject 24. Such a scanner system is in fact depicted in U.S. Pat. No. 4,630,202 to Mori (Dec. 16, 1986), which describes a third generation system. Similarly, in the other configurations described above, the moving source of X-ray beams or fan beams could be produced by rotating an X-ray source of such beams, or by scanning a stationary X-ray emitting target with a moving electron beam (as is done in FIG. 1E).

FIG. 2 is a detailed depiction of the contents of the DAS 30 in FIG. 1E, and depicts a prior art technique for reducing the number of A/D converters and resultant digitalized information channels that require computer processing. FIG. 2 also depicts several relationships required to reconstruct an image from CT data.

In the center of FIG. 2 is shown the isocenter 21 for a scanner system 10. By definition, the isocenter is the center of a fictitious image reconstruction circle 23, within whose circumference must lie the object O to be scanned and suitably reconstructed. Further, isocenter 21 is also the center of the array 25 of the detectors $D_i$, and the center of the X-ray beam source or scan path 27 (which coincides with target 18 in the embodiment of FIG. 1E). For acceptable reconstruction, the region within the circle 23 must be exposed to X-ray beams from all possible directions.

The depiction of FIG. 2, wherein the vortex of the beam fans shown is a source point is termed a "source fan". In a source fan depiction, it is understood that at any given time, an X-ray fan beam simultaneously strikes many detectors. Although for ease of illustration only two X-ray fan beams are shown, each having three beams, a fan beam such as $B_t$ is actually a continuum comprising a large number of X-ray beams.

The relationship between the isocenter, the image reconstruction circle, the location of the detector(s) and X-ray source or X-ray beam source exists for any of the systems shown in FIGS. 1A–1E. While FIG. 2 depicts the X-ray source or X-ray beam source as being radially more distant from the isocenter than the detectors, the converse could be true, or in a suitable arrangement equal distances could be employed. Any of the CT systems shown in FIGS. 1A–1E can suitably reconstruct any image 0 lying within the reconstruction circle 23. Note in FIG. 2 that the lower ends of the detector array 25 extend at least to (and preferably slightly beneath) the lower edge of the reconstruction circle 23, while the upper ends of the scan path 27 extend to (and preferably slightly above) the upper edge of the reconstruction circle 23. This configuration ensures that any point within circle 23 is scanned from every possible direction (including horizontally), and that all X-ray beams fall at least partially on a portion of the detector array 26.

Detector array 26 in FIG. 1E preferably may include as many as 4,800 detectors (or detector positions) spaced apart a distance d about 1 mm or 0.1° (see FIG. 3). However for ease of illustration only nine such detectors ($D_1$, $D_2$, ... $D_9$) are depicted in FIG. 2, disposed along arc 25. Because the X-ray fan beam 22 is depicted by arrow 28 as moving clockwise, it is understood that detector $D_1$ is scanned first by the beam 22, then detector $D_2$, $D_3$ and so forth. For example, at an arbitrary time t, a fan beam $B_t$ is emitted at a position $S_t$ along the tungsten target 18 (see FIG. 2). A short time later, the electron beam 14 (see FIG. 2) scans position $S_{t+1}$ along the target 18 and a fan beam $B_{t+1}$ results. The result is a scanning fan beam B that sweeps clockwise along arc 27 in FIG. 2. Depending upon mode of operation, for the system of FIG. 1E the electron beam 18 preferably scans about 210° along the target 18 in perhaps 50 mS to 100 mS.

For ease of illustration, FIG. 2 does not depict the current to voltage conversion ("I/V") for each detector output, or any filtering to limit higher frequency detector output components. At any given time, only detectors exposed to the moving X-ray fan beam 22 need be activated or read. For a system such as that shown in FIG. 1E having about 2,000 detectors, a given detector is activated and its output sampled every 10 $\mu$s to every 50 $\mu$s or so. This selective detector activation, preferably controlled by computer system 32, promotes efficient signal processing because time is not wasted sampling detectors having no meaningful output to contribute to the reconstructed image.

Because they are not simultaneously read or A/D converted, detectors $D_1$, $D_2$, and $D_3$ may be multiplexed together using multiplexer 40, whose single analog output is digitized with an A/D converter 42. Similarly, outputs from detectors $D_4$, $D_5$, $D_6$ and $D_7$, $D_8$, $D_9$ may be multiplexed using multiplexers 44 and 48, respectively, whose single outputs are then digitized by A/D converters 46 and 50, respectively. It is of course not necessary that the multiplexed detectors be adjacent to each other, only that they not be simultaneously converted.

Thus, in the example depicted in FIG. 2, by multiplexing the output from three detectors, the number of required A/D converters is reduced to one-third. In a CT system with about 4,800 detectors, the use of multiplexers can reduce the number of required A/D converters from about 4,800 to about 1,700. Unfortunately providing a CT system with 1,700 A/D converters is still rather expensive, and still represents approximately 1,700 channels of digitized signal data to be computer processed downstream.

Different multiplexing schemes can of course reduce the number of A/D converters (and thus the number of digitized information channels requiring processing) by a factor greater than three. However aside from such multiplexing techniques, it is not known in the art how to further reduce the number of A/D converters without substantial degradation of the resultant CT system video image. For example, conventional wisdom has long considered it unfeasible to directly combine the outputs of two or more detectors without loss of image resolution due to degradation of the detector modulation transfer function ("MTF").

To recapitulate, what is needed is an apparatus and method for combining detector output signals in a CT system that not only reduces the number of information channels to be processed (using multiplexers) but also reduces the complexity of the A/D conversion circuitry and the associated delay and combining circuitry. Additionally, it is important that such apparatus and method should not substantially degrade the resultant video image, should be relatively inexpensive to implement, and preferably should operate in real time in a conventional CT system. The present invention discloses such an apparatus and method.

SUMMARY OF THE INVENTION

In a first aspect, the present invention provides a method for reducing the complexity of A/D converters and downstream processing in a CT system and includes digitally combining two or more detectors into a pseudo detector, whose single output is then processed for forming a CT image. A pseudo detector is created by digitally summing together the output data read from two or more detectors that receive X-ray beams having substantially the same Radon radius and preferably passing through substantially the same region of the reconstruction circle within the CT system. Alternatively, the pseudo detector can be created from a single detector that is sequentially repositioned. More specifically, the digital data output signal from the pseudo detector comprises a data bit stream having M-bit wide digital data signals whereas the signal processing leading up to generating this data output signal from the pseudo detector uses digital data words having less than M-bit width. That is, a bit stream means is responsive to each of the detector analog output signals, for providing respective K-bit wide data bit streams, where K is less than M (and preferably is equal to one). Each of the K-bit wide data bit streams is representative of amplitude changes of a corresponding one of the detector analog output signals. At least one digital delay means, responsive to at least one of the K-bit wide data bit streams, establishes a predetermined relative time delay between the K-bit data wide bit streams. A digital combining means, responsive to the K-bit wide data bit streams having the relative time delay established therebetween, sums said K-bit wide data bit streams and forms a single, M-bit wide data bit stream.

In the preferred embodiments, the bit stream means includes a delta sigma A/D converter so as to provide the reduced width bit stream representative of the analog signals. In a first one of the preferred embodiments, which uses components that are presently commercially available, a delta sigma converter receives an amplified and level shifted analog signal from each x-ray detector and provides on a serial output (that is, a one bit wide bit stream) multi-bit digital words representative of amplitude changes of the analog signals. A simple digital delay device, such as a shift register, can then be used for simply and reliably establishing a time delay between the single bit wide bit streams in the signal processing channels for adjacent detectors. Additionally, a relatively simple digital combining means can be used for adding together the single bit wide bit stream for adjacent detector channels for forming the multi-bit wide bit streams which are then processed in the conventional manner for developing the CT image.

In a further embodiment of the invention, a current sensitive modulator portion of the delta sigma A/D converter is separated from its filtering section, so that amplification and level shifting circuitry is not required at the input to the delta sigma modulator. This greatly reduces the circuit complexity of the signal processing circuitry. Delay means is then coupled to the output of the delta sigma modulator for providing a time delay between adjacent detector signal processing channels. At this point, the reduced-width bit streams can be combined, registered and offset corrected as in the previously described embodiment, or alternatively, multibit width digital words can be formed for each detector signal processing channel by digital low pass filtering and decimation. Alternatively, depending upon the trade-off among the cost of the circuit components, the speed of the A/D converter and the resolution required for the system, the digital low pass filtering and decimation could occur after the adjacent detector channels have been combined, or the digital filtering can be apportioned so as to be partially before and after the adjacent detector channel combining.

Whether the X-ray beams are received by different detectors at different times, or by a single detector at different locations at different times, the delaying step is as follows. If the detector array comprises N preferably adjacent detectors or detector locations, then relative to the last (or Nth)-read detector, the output from each earlier read detector is delayed a time $(N-i)\tau$. In this relationship, i is the number of the detector ($1 \leq i \leq N$) and $\tau$ is the time it takes the X-ray source to move an angular distance equal to the angular distance between adjacent detectors (or detector locations). The output from the first-scanned detector (i=1) is delayed a time $(N-1)\tau$, the output from the second-scanned detector (i=2) is delayed a time $(N-2)\tau$, and so on, with the output from last-scanned detector (i=N) receiving zero delay.

In a second aspect, the present invention provides an apparatus implementing the above method by digitally summing together detector outputs that correspond to X-rays that have substantially the same Radon radius and preferably pass through substantially the same region of the CT system reconstruction circle. Such X-ray beams may be received by different detectors at different locations and times, or by a single detector at different locations at different times.

In either aspect, the present-invention provides a reconstructed CT video image substantially without degradation. While more than two detectors can be combined in a pseudo detector, the quality of the reconstructed image is preserved when the number of detectors comprising a pseudo detector is small. Having a small number of combined detectors promotes close proximity of the detectors or detector positions comprising the pseudo detector, and ensures that data obtained from each detector represent an X-ray beam passing through substantially the same region of the CT system reconstruction circle.

Other features and advantages of the invention will appear from the following description in which the preferred embodiments have been set forth in detail in conjunction with the accompanying drawings.

DESCRIPTION OF THE PREFERRED EMBODIMENTS

The present invention reduces the complexity of the A/D converters in a CT system by combining two or more detector outputs to create a pseudo detector, whose single output is then processed. Alternatively, a pseudo detector according to the present invention can combine multiple outputs from a single detector that is sequentially repositioned. Contrary to conventional wisdom, applicant has discovered that an image reconstructed from the output of pseudo detectors will not be substantially degraded.

According to the present invention, a pseudo detector is implemented by creating narrow-width bit streams representative of the analog output read from detectors that see X-ray beams having substantially the same Radon radius, which beams preferably see substantially the same region of the object under examination, establishing a time delay between the detector outputs, and then combining the detector outputs to form a relatively wide bit width bit stream. For cylindrically symmetrical objects under examination (e.g., a perfect tree log) applicant's pseudo detectors provide an exact method, even if the detectors (or detector positions) are widely spaced. For other objects, the method is inexact but acceptable, especially where the detectors forming the pseudo detector are in relatively close proximity to one another so that substantially the same X-ray beam is received by each detector.

U.S. Pat. No. 4,066,900 issued Jan. 3, 1978 to Mr. LeMay generally discloses the technique of combining A/D converted output signals from adjacent detectors in a CT imaging system, with an appropriate time delay therebetween. Thus, no further discussion concerning the theory behind such combination appears to be required to explain this basic concept.

Various implementations of the present invention will now be described with reference to FIGS. 3-5. As noted, the delay time $\tau$ is a function of the geometry of detector arc 25, the location of the detectors (or detector positions) comprising detector array 26 along that arc, the geometry of the X-ray source arc 27, and the rapidity with which the X-ray source is moved along arc 27. The desired delay time $\tau$ (or delay times if $\tau$ is not a constant) is known, and preferably is maintained within about ±5% to minimize image degradation according to the present invention.

Figure 1D:
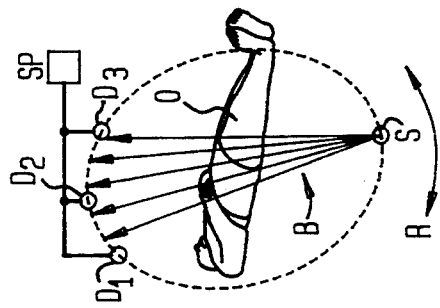
FIG. 1D depicts the configuration of a fourth generation CT scanning system, with which the present invention may be practiced.
Figure 1C:
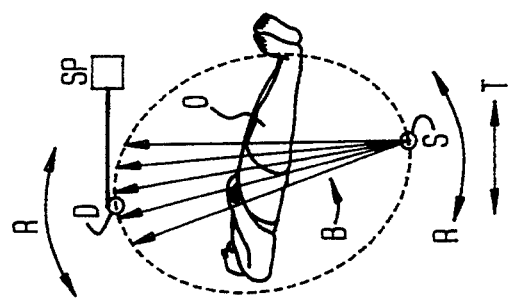
FIG. 1C depicts the configuration of a third generation CT scanning system, with which the present invention may be practiced.
Figure 1B:
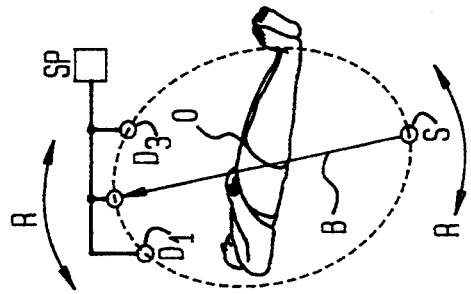
FIG. 1B depicts the configuration of a second generation CT scanning system, with which the present invention may be practiced.
Figure 1A:
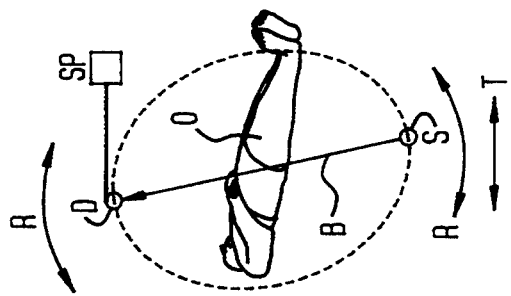
FIG. 1A depicts the configuration of a first generation CT scanning system, with which the present invention may be practiced.
Figure 1E:
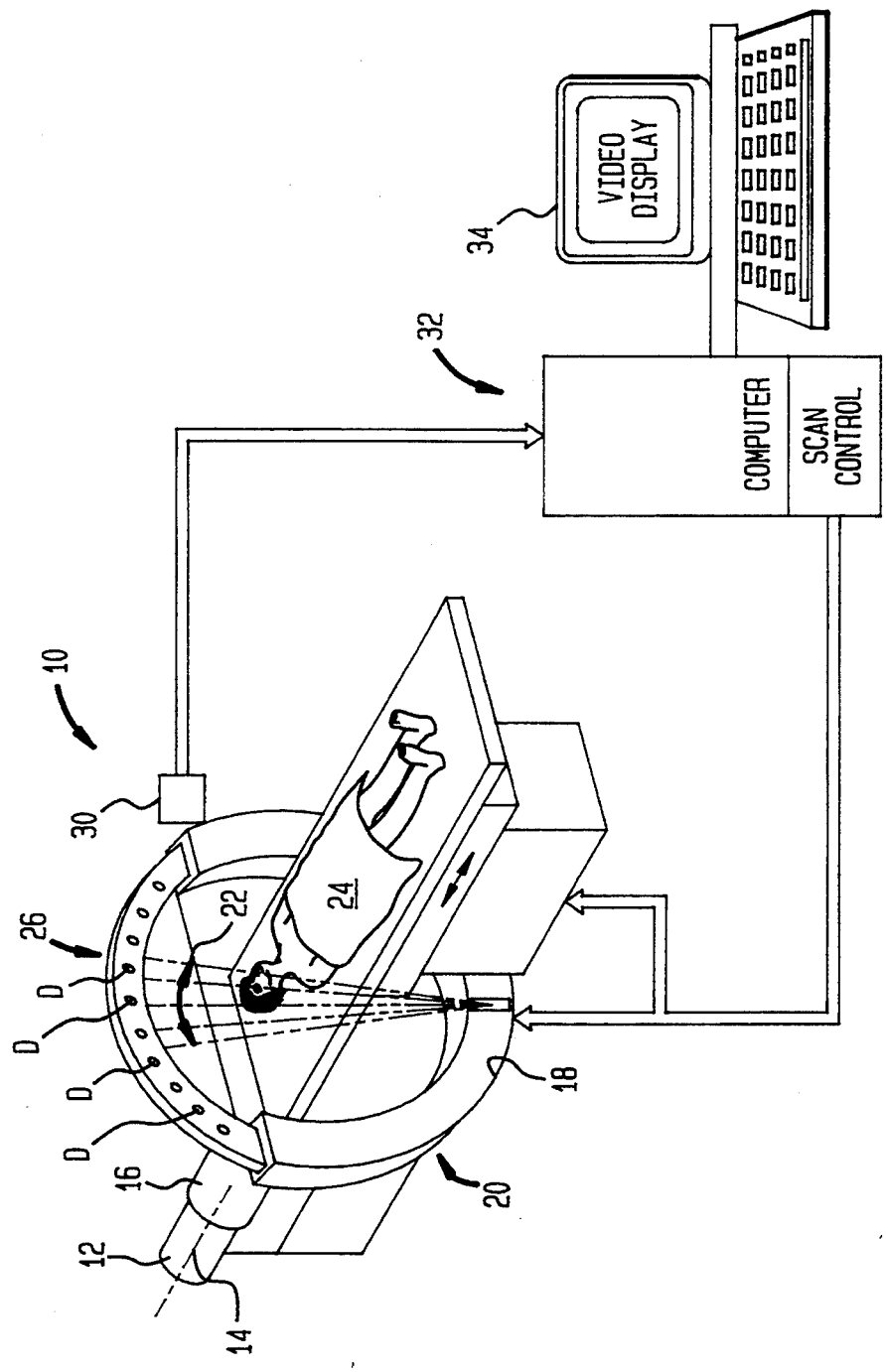
FIG. 1E depicts in detail a fourth generation scanning electron beam CT system, with which the present invention may be practiced.
Figure 2:
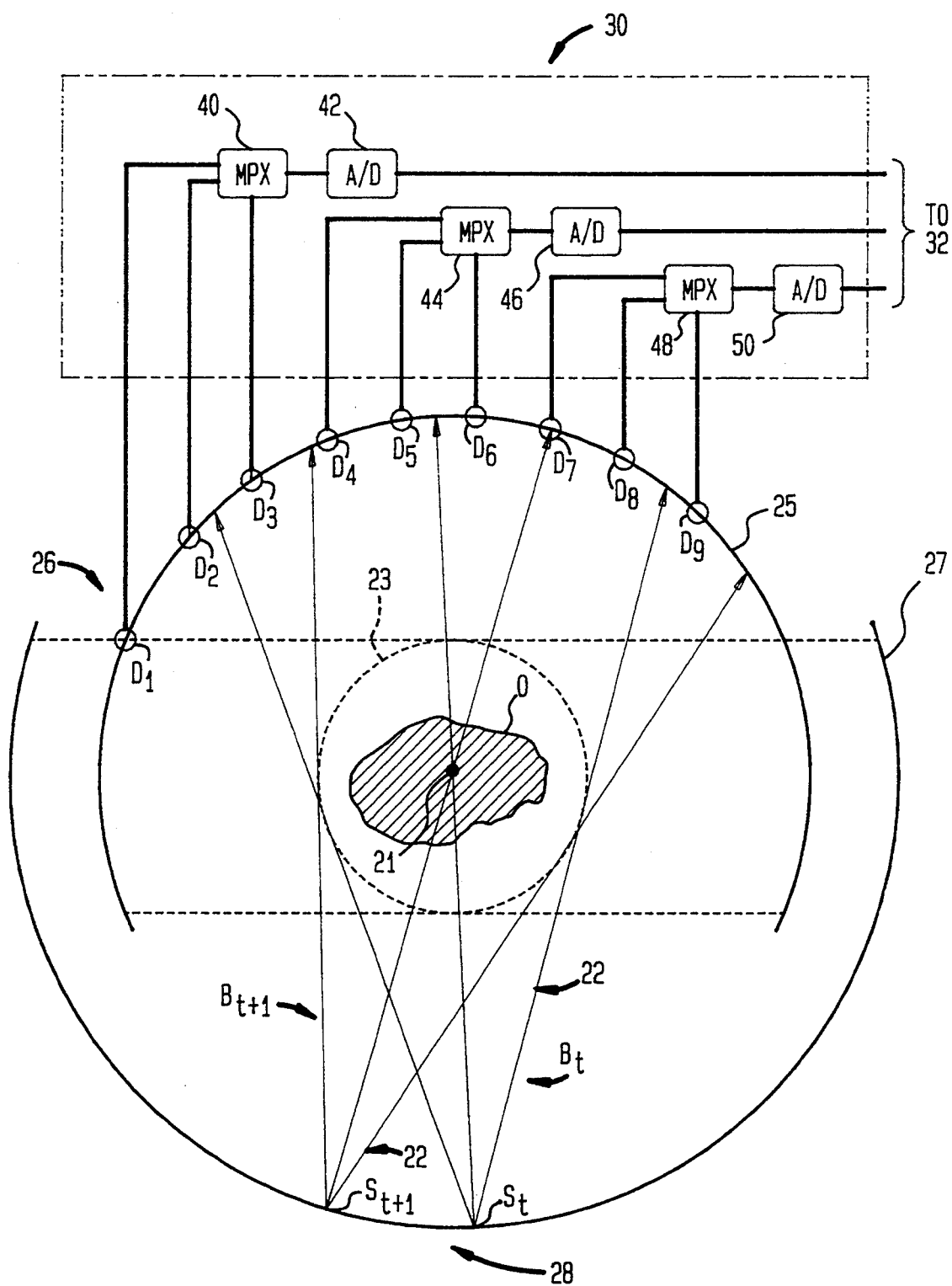
FIG. 2 depicts multiplexing detector outputs to reduce the number of A/D converters and the number of digitized signal channels requiring computer processing, according to the prior art.
Figure 3:
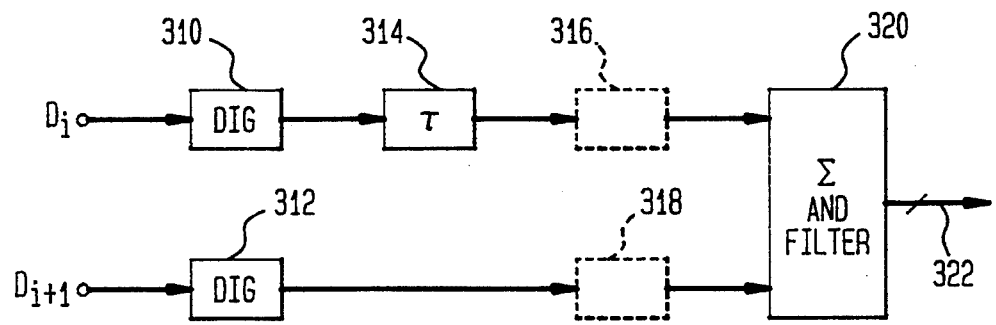
FIGS. 3-5 depict the digitization and summation of two detector outputs, according to various embodiments of the present invention.

FIG. 3 is a basic block diagram for a digital acquisition system (DAS) for use as a replacement for box 30 in a system such as shown in FIG. 2.

In FIG. 3 adjacent detectors $D_i$ and $D_{i+1}$ (where i equals the number of the detector, i equals 1 through N, and N being the total number of detectors in detector array 26) are digitized so as to produce relatively narrow bit width streams representative of the detector analog signals. In accordance with the invention, the digitization is accomplished using delta sigma A/D converters 310 and 312, which each provide a digital output bit stream having a bit width which is substantially less than the bit width developed for each detector signal in accordance with the prior art. A digital time delay means 314 establishes the required time delay ($\tau$) between the adjacent signals. Due to the narrow width bit stream for each channel, the time delay means 314 can be realized using a relatively simple, reliable and low cost digital circuit, such as a N-bit wide shift register, where N equals the width of the narrow bit stream provided by digitizer 310. As with all delta sigma A/D converters, digital-filtering is necessary to realize the wide or full bit width digital output words. Thus, before and/or after and/or during the digital combining of the digitized adjacent detector signals FIR filters and appropriate decimation circuitry can be utilized, such as illustrated by optional digital filtering circuits 316 and 318. Since noise filtering and signal shaping of the x-ray detector signals is required in any event, such filtering can be conveniently combined and incorporated into the digital filtering necessary for completing the delta sigma A/D converter, thereby resulting in a negligible increase in the digital circuitry required to accomplish the present invention, as compared with the prior art. Additionally, since in the present invention the filtering is done in the digital domain, symmetric impulse response signal shaping is possible, as compared with the less desirable asymmetrical signal shaping performed by the analog filters of the prior art embodiments. The output of the signal combiner and filter circuit 320 is then a full bit width digital word representation of the combined adjacent detector signals (the pseudo detector) whose single output signal on line 322 may thereafter be processed as in the prior art for developing the CT images. The circuitry required for combining the reduced bit width bit streams comprises a relatively simple adder circuit and the digital filtering aspects of combiner 320 comprise recursive filters such as those commonly used in delta sigma A/D converters, as well known to those skilled in the art. Such filters are also described, for example, in application note "AN10REV1" from Crystal Semiconductor Corporation of Austin, Tex. entitled "Delta-Sigma Techniques". One commercially available integrated circuit useful for accomplishing such delta-sigma A/D conversion is No. CS5338 A/D Converter available from Crystal Semiconductor Corporation.

Figure 4:
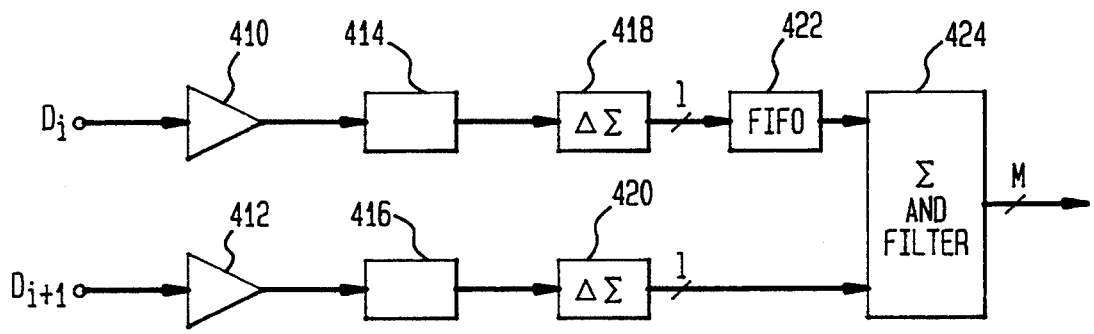

FIG. 4 illustrates an embodiment using currently available components.

The signal currents from the detectors $D_i$, and $D_{i+1}$ are converted to single ended voltages by current to voltage transimpedance amplifiers 410 and 412. Those signals are then converted to bipolar signals ($\pm V$) by analog gain and level shifter circuitry 414 and 416, which bipolar signals are then applied as input signals to two delta-sigma A/D converters 418 and 420. A/D converters 418 and 420 may comprise Model No. CS5338 A/D Converters available from Crystal Semiconductor Corportion.

In this implementation, time delay ($\tau$) is accomplished by using the digital power-down command of the A/D converter chip (pin 10 of ICCS5338). Thus, the same clock can be used to drive all of the A/D converters in the DAS. More specifically, after A/D converters 418 and 420 are put into the power-down mode, converter 418 is put into the active state, which starts an internal calibration cycle having exactly m clock cycles. The power-up (or release) of converter 420 is delayed by the desired delay time ($\tau$) to be established between the adjacent detectors, which then starts exactly the same calibration cycle as in converter 418. Thus, the first conversion from converter 418 will be exactly the desired time delay apart from the first one of converter 420. As soon as the first conversion from converter 420 is read into a combiner 424, the combiner reads the first conversion output from converter 418, which was held in a temporary storage device 422, such as a FIFO. Combiner 424 also provides offset correction, as necessary, which offsets one inherent in A/D conversion.

Note, FIFO 422 acts as a buffer to hold the output of converter 418 until the delayed output from converter 422 is ready to be added to it via combining circuitry 424. Additionally, the digital filtering and decimation which is conventional for A/D converters of the delta-sigma type, is included within converters 418 and 420 and their outputs each comprise a serial bit stream of, for example, 16-bit words. As previously noted, the digital filtering used in converters 418 and 420 advantageously includes that filtering conventionally necessary in CT detector channel processing.

Figure 5:
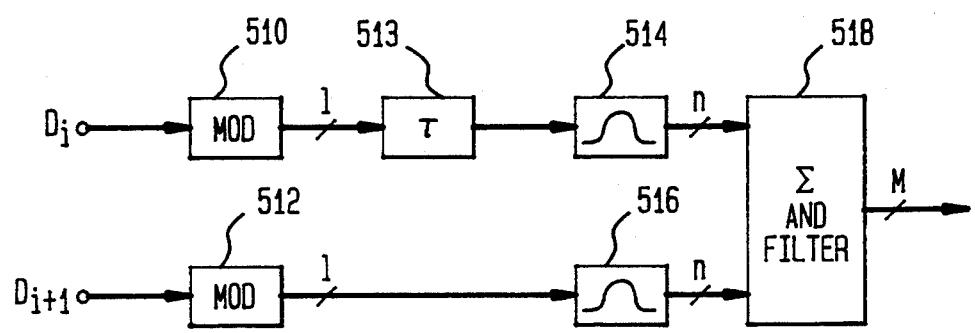

FIG. 5 illustrates a more cost-efficient circuit topology for the present invention. In this embodiment the modulator portion of the A/D converter is separated from the filtering portion, so that a simple one-bit wide shift register can be used for establishing the time delay, tau. Additionally, detector output signals $D_i$ and $D_{i+1}$ are connected so as to directly provide a current input to the modulator portion of a delta sigma modulator, such as the modulator described in the forenoted "Application Note AN10REV1" which is used in the delta-sigma A/D converters available from Crystal Semiconductor Corporation. Thus, the transimpedance amplifiers and analog gain and level shifting circuitry required in the FIG. 4 embodiment, are not necessary in this preferred embodiment. After establishing the appropriate time delay between the signal in the adjacent detector channels, the user must decide how much filtering is desirable to be accomplished before the bit streams of the adjacent channels are combined. As illustrated in FIG. 5, impulse response filtering (such as a digital low-pass filter) and decimation is provided for each bit stream by digital filters 514 and 516. The filter outputs are then applied to a digital combining circuit 518 for providing an M-bit wide output signal for further processing and developing of the CT image. Due to cost constraints and a users trade-off between resolution (bit width) and digitizing rate, the amount of digital filtering and decimation which occurs before and/or after signal combiner 518 can vary. Thus, more specific guidelines concerning the bit width (n) of the signals provided into combiner 518 cannot be given.

In conclusion, for a given amount of dollars a prior art CT system will typically employ a certain number of detectors and A/D converters. For the same dollar budget, the present invention enables a CT system to be constructed with considerably more detectors but with less complex A/D converters and downstream processing components, the result being a superior quality reconstructed image. Alternatively, for a given quality image, the present invention enables a CT system to be built for fewer dollars by using the same number of detectors as an existing system, but with less complex A/D converters and fewer downstream processing components, the result being a more competitively priced system.

It will be apparent to those of ordinary skill in the art that modifications and variations may be made to the disclosed embodiments without departing from the subject and spirit of the invention. For example, the invention can be used in conjunction with the multiplexing technique of FIG. 2 to reduce the number of processing channels by an additional two-thirds. All such changes, modifications, variations and other uses and applications which do not depart from the spirit and scope of the invention are deemed to be covered by the invention which is limited only by the claims which follow.

What is claimed is:

1. In a computed tomography X-ray system having an X-ray source causing at least one X-ray beam to traverse at least a region of a reconstruction circle and be detected by at least two detectors for developing analog detector output signals which are processed in a plurality of signal processing channels for reconstructing an image of said reconstruction circle, and a combining means for combining output signals read from said detectors, which signals correspond to x-ray beams having a substantially same Radon radius, a combining means for reducing the complexity of said plurality of signal processing channels without substantially degrading said image, comprising:

a sigma-delta modulator for digitizing successive samples of each of the output signals into a one-bit wide stream of successive digital output signals, each bit of said stream being representative of an amplitude change from its preceding bit and not representative of an absolute amplitude level for a sample of said output signal;

a one-bit wide digital delay for establishing a time delay $(N-i)\tau$ between at least two streams of digital output signals developed from the output signals of at least two of said detectors, wherein i=1 represents a first-read detector, i=N represents a last-read detector and $1 \leq i \leq N$, and wherein $\tau$=the time between reading spatially adjacent ones of said detectors i and i+1; and a digital combining means, responsive to said at least two streams of digital output signals having said time delay established therebetween, for combining said streams of digital output signals and forming a combined output signal representative of both said streams of digital output signals which are combined, said combined output signal having a bit-width greater than one, and representative of an absolute amplitude level of a sample of said output signals without reference to other samples of said output signals, said combined output signals being used for reconstructing said image.

2. The CT system of claim 1, wherein:

said digital delay comprises a first-in, first-out digital shift register type memory device.

3. The CT system of claim 1, wherein:

a sigma-delta modulator is provided in each of said signal processing channels.

4. The CT system of claim 3, wherein:

a digital filter means is coupled to the output of each of said sigma-delta modulators for providing in a parallel manner digital signals which have a bit-width greater than one; and said digital delay is coupled between the output of said sigma-delta modulators and the input of said digital filter means.

5. The CT system of claim 4, wherein:

said sigma-delta modulators are direct current coupled to receive the analog output signals developed from each of said detectors.

6. The CT system of claim 4, wherein said digital combining means includes:

a one-bit wide digital adder for combining said at least two output signals having a time delay established therebetween, for forming combined output signals; and a first digital filter coupled to the output of said adder for developing from said combined output signals a multi bit-width output signal for use in reconstructing an image of said reconstruction circle.

7. The CT system of claim 6 wherein:

a second digital filter means is coupled to the output of each of said sigma-delta modulators for providing in a serial manner a plurality of one-bit wide digital signals, where at least two serially provided ones of said one-bit wide digital signals correspond to the same detector output signal sample; and said digital delay is coupled between the output of said signal delta modulator and said second filter means.

8. The CT system of claim 7, wherein:

said second digital filter means comprises a digital FIR filter and decimator.

9. The CT system of claim 8, wherein:

said digital delay comprises a first-in, first-out digital shift register type memory device.

10. The CT system of claim 3, wherein:

said digital filter means comprises a digital FIR filter and decimator.

11. The CT system of claim 3, wherein:

said sigma-delta modulators are direct current coupled to receive the analog output signals developed from each of said detectors.

* * * * *